US00PP13369P2

(12) United States Plant Patent
Dümmen

(10) Patent No.: US PP13,369 P2
(45) Date of Patent: Dec. 17, 2002

(54) POINSETTIA PLANT NAMED 'DUENIBRIRED'

(75) Inventor: Marga Dümmen, Rheinberg (DE)

(73) Assignee: Dümmen Jungpflanzenkulturen, Rheinberg (DE)

( * ) Notice: Subject to any disclaimer, the term of this patent is extended or adjusted under 35 U.S.C. 154(b) by 0 days.

(21) Appl. No.: 09/996,388

(22) Filed: Nov. 30, 2001

(51) Int. Cl.[7] ..... A01H 5/00

(52) U.S. Cl. ..... Plt./307

(58) Field of Search ..... Plt./307, 306

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Duenibrired', characterized by its inflorescences with inflorescences with bright red-colored flower bracts; dark green-colored leaves with red purple-colored petioles; uniform and rounded plant habit; freely branching habit; early flowering; and excellent post-production longevity.

1 Drawing Sheet

BOTANICAL CLASSIFICATION/CULTIVAR DENOMINATION

*Euphorbia pulcherrima* Willd. cultivar Duenibrired.

BACKGROUND OF THE INVENTION

The present Invention relates to a new and distinct cultivar of Poinsettia plant, botanically known as *Euphorbia pulcherrima* Willd., and hereinafter referred to by the name 'Duenibrired'.

The new Poinsettia is a product of a planned breeding program conducted by the Inventor in Rheinberg, Germany. The objective of the breeding program is to create new Poinsetta cultivars with uniform plant habit and attractive flower bract coloration.

The new Poinsettia originated from a cross made by the Inventor of a proprietary selection of *Euphorbia pulcherrima* Willd. identified as code number AA 96, not patented, as the female, or seed, parent, with a proprietary selection of *Euphorbia pulcherrima* Willd. identified as code number EE 94, not patented, as the male, or pollen parent. The cultivar Duenibrired was discovered and selected by the Inventor as a flowering plant within the progeny of the stated cross in a controlled environment in Rheinberg, Germany. The selection of this plant was based on its attractive flower bract coloration and uniform plant habit.

Asexual reproduction of the new Poinsettia by vegetative terminal cuttings taken at Rheinberg, Germany, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duenibrired'. These characteristics in combination distinguish 'Duenibrired' as a new and distinct cultivar:

1. Inflorescences with bright red-colored flower bracts.
2. Dark green-colored leaves with red purple-colored petioles.
3. Uniform and rounded plant habit.
4. Freely branching growth habit.

5. Early flowering; response time, about eight weeks.
6. Excellent post-production longevity.

Compared to plants of the female parent, the selection AA 96, plants of the new Poinsettia have darker green and smoother leaves and have longer postproduction longevity. Compared to plants of the male parent, the selection EE 94, plants of the new Poinsettia have more cyathia per corymb.

Plants of the new Poinsettia can be compared to plants of the cultivar 490, disclosed in U.S. Plant Pat. No. 7,825. In side-by-side comparisons conducted in Rheinberg, Germany, plants of the new Poinsettia differed primarily from plants of the cultivar 490 in the following characteristics:

1. Plants of the new Poinsettia were slightly taller and had slightly longer lateral branches than plants of the cultivar 490.
2. Plants of the new Poinsettia had larger leaves than plants of the cultivar 490.
3. Plants of the new Poinsettia had slightly smaller flower bracts than plants of the cultivar 490.
4. Plants of the new Poinsettia had larger cyathia clusters and more cyathia per corymb than plants of the cultivar 490.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia.

The photograph comprises a side perspective view of a single flowering plant of 'Duenibrired' grown in a container.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Rheinberg, Germany during the winter under commercial practice in a glass-covered greenhouse with day and night temperatures about 22° C. and light levels about 4,500 foot-candles. Single plants were grown in 14-cm pots and pinched once. Plants were flowered under natural season short day/long night conditions. Plants were about 16 weeks from unrooted cuttings when the photographs and the detailed botanical description were taken.

In the following description, color references are made to The Royal Horticultural Society Colour Chart, 1995 edition, except where general terms of ordinary dictionary significance are used.

Botanical classification: *Euphorbia pulcherrima* Willd. cultivar Duenibrired.

Parentage:

*Female parent.*—Proprietary selection of *Euphorbia pulcherrima* Willd. identified as code number AA 96, not patented.

*Male parent.*—Proprietary selection of *Euphorbia pulcherrima* Willd. identified as code number EE 94, not patented.

Propagation:

*Type cutting.*—Vegetative terminal cuttings.

*Time to initiate roots.*—Summer: About 9 days at 22° C. Winter: About 13 days at 22° C.

*Time to develop roots.*—Summer: About 21 days at 22° C. Winter: About 28 days at 22° C.

*Root description.*—Thick, fibrous and freely-branching.

Plant description:

*Plant form.*—Inverted triangle, top of plant rounded.

*Growth habit.*—Upright and uniform plant habit.

*Plant height.*—About 21 cm.

*Plant diameter or spread.*—About 47 cm.

*Lateral branch description.*—Quantity per plant: About ten lateral branches develop after pinching. Length: About 17 cm. Diameter: Less than 1 cm. Internode length: About 1.25 cm. Color: 137B.

*Foliage description.*—Arrangement: Alternate, single. Quantity of leaves per lateral branch: About twelve. Length: About 11 cm. Width: About 7.5 cm. Shape: Mostly ovate with irregular lobing. Apex: Acuminate to apiculate. Base: Obtuse. Margin: Entire with irregular lobing. Venation pattern: Pinnate. Texture, upper and lower surfaces: Glabrous. Surface: Mostly flat. Color: Young foliage, upper surface: 135B. Young foliage, lower surface: 141B. Fully expanded foliage, upper surface: 136A. Fully expanded foliage, lower surface: 141A. Venation, upper surface: 152A. Venation, lower surface: 144B. Petiole: Length: About 5.7 cm. Diameter: About 3 mm. Texture: Glabrous. Color, upper and lower surfaces: 59A.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Response time, about eight weeks.

*Post-production longevity.*—Plants of the new Poinsettia maintain good substance and bract color for about eight weeks under interior conditions and about 12 to 14 weeks under greenhouse conditions.

*Quantity of inflorescences per plant.*—One per lateral branch, about ten.

*Inflorescence size.*—Diameter: About 21 cm. Height (depth): About 3 cm.

*Flower bracts.*—Quantity of flower bracts per inflorescence: About 15. Length, largest bracts: About 8.5 cm. Width, largest bracts: About 5.3 cm. Shape: Mostly ovate with irregular lobing. Apex: Acuminate to apiculate. Base: Obtuse. Margin: Entire with irregular lobing. Texture, upper and lower surfaces: Glabrous, velvety. Surface: Rugose. Orientation: Mostly horizontal. Color: Developing bracts, upper surface: 53A. Developing bracts, lower surface: 46A. Fully developed bracts, upper surface: 46C; color fading to 45D with subsequent development. Fully developed bracts, lower surface: 46D. Venation, upper and lower surfaces: Same as lamina. Bract petiole: Length: About 4.5 cm. Diameter: About 2.5 mm. Texture: Glabrous. Color: 59A.

*Cyathia.*—Quantity of cyathia per corymb: About 15. Diameter of cyathia cluster: About 3 cm. Length: About 7 mm. Diameter: About 4 mm. Shape: Ovoid. Color: Immature: 144C. Mature: 144B. Peduncle: Length: About 5 mm. Diameter: Less than 1 mm. Strength/aspect: Moderately strong, curved. Color: 144B. Stamens: Quantity of stamens per cyathium: About 15. Anther shape: Oval. Anther length: About 0.4 mm. Anther color: 31A. Amout of pollen: Moderate. Pollen color: 14A. Pistils: Quantity of pistils per cyathium: One. Pistil length: About 8 mm. Style length: About 3 mm. Style color: 53B. Stigma color: 59A. Nectaries: Quantity of nectaries per cyathium: One. Color: 17C.

Disease/pest resistance: Resistance to pathogens and pests common to Poinsettias has not been observed on plants grown under commercial conditions.

It is claimed:

1. A new and distinct cultivar of Poinsettia plant named 'Duenibrired', as illustrated and described.

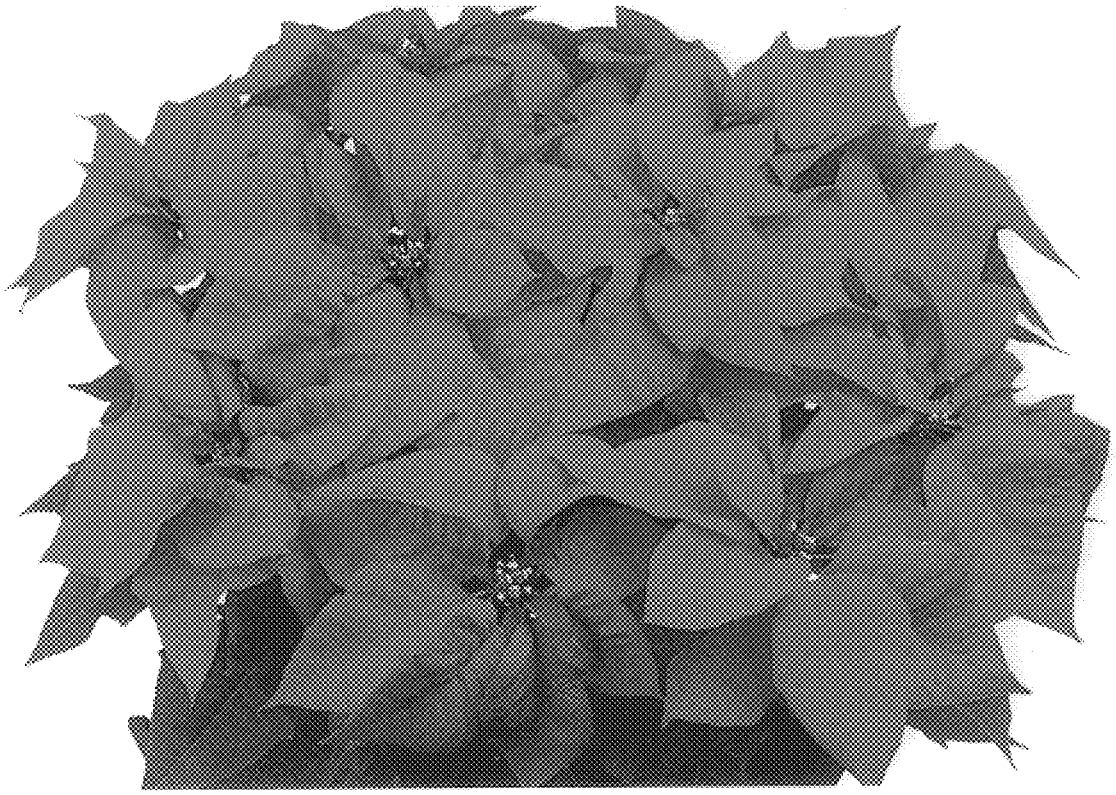

* * * * *